(12) United States Patent
Barrow et al.

(10) Patent No.: US 7,901,927 B1
(45) Date of Patent: Mar. 8, 2011

(54) TRANSFER AND INCORPORATION OF HERITABLE SYMBIOTIC FUNGI INTO NON-HOST PLANTS

(75) Inventors: Jerry R. Barrow, Fairacres, NM (US); Mary E. Lucero, Las Cruces, NM (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 893 days.

(21) Appl. No.: 11/500,702

(22) Filed: Aug. 8, 2006

Related U.S. Application Data

(60) Provisional application No. 60/706,648, filed on Aug. 9, 2005.

(51) Int. Cl.
*C12N 1/00* (2006.01)
(52) U.S. Cl. ........................ 435/254.1; 435/410; 435/430
(58) Field of Classification Search ................... 435/410, 435/430, 254.1
See application file for complete search history.

(56) References Cited

U.S. PATENT DOCUMENTS 5,723,720 A * 3/1998 Brede et al. .................. 800/298
2004/0082474 A1* 4/2004 Henson et al. ................ 504/117

OTHER PUBLICATIONS

Vierheilig et al. "Spreading of *Glomus mosseae*, a vesicular-arbuscular mycorrhizal fungus, across the rhizosphere of host and non-host plants," Soil Biol. Biochem, vol. 27, No. 8, pp. 1113-1115, 1995 (3 pages total).*
Barrow et al. "Fungal endophytes intrinsically associated with micropropagated plants regenerated from native *Bouteloua eriopoda* Torr. and *Atriplex canescens* (Pursh) Nutt.," In Vitro Cell. Dev. Biol.-Plant 40:608-612, Nov.-Dec. 2004.*
Redman, Regina S., et al., "Thermotolerance Generated by Plant/Fungal Symbiosis", Science, vol. 298, Nov. 22, 2002, p. 1581.
Johnson-Cicalese, J., "Cross Species Inoculation of Chewings and Strong Creeping Red Rescues with Fungal Endophytes", Crop Sci, 40, pp. 1485-1489, Sep.-Oct. 2000.
Johnson, Mark C. et al., "Infection of Tall Fescue with *Acrenomium coenophialumby* Means of Callus Culture", Plant Disease, vol. 70, No. 5, 2986 pp. 380-382.

* cited by examiner

*Primary Examiner* — Susan B. McCormick Ewoldt
(74) *Attorney, Agent, or Firm* — John Fado; Randall E. Deck; Lesley Shaw

(57) ABSTRACT

A first plant species or a part thereof may be produced which has stably and heritably integrated therein one or more endophytic fungi which are derived from a second, different plant species. This first plant species is not a host plant for the endophytic fungi in nature. These resultant first plant species containing the endophytic fungi exhibit substantially increased vigor, altered morphology and chemistry, and increased reproductive potential compared to non-treated controls.

13 Claims, 14 Drawing Sheets

TRANSFER AND INCORPORATION OF HERITABLE SYMBIOTIC FUNGI INTO NON-HOST PLANTS

CROSS-REFERENCE TO RELATED APPLICATIONS

This application claims the benefit under 35 U.S.C. 1.19(e) of U.S. provisional patent application No. 60/706,648, filed Aug. 9, 2005, the contents of which are incorporated by reference herein.

BACKGROUND OF THE INVENTION

1. Field of the Invention

The invention relates to a novel method for transferring and integrating endophytic fungi to non-host plants as heritable components.

2. Description of the Prior Art

In recent decades, the development of improved technologies for examining microscale communities of plant-associated fungi has contributed to increasing appreciation for the roles these organisms play in larger scale ecosystems. Using light and electron microscopy, chemical analysis, and molecular markers, it is now possible to detect and quantify the complex microbial communities inhabiting not only soils, but individual plants. For example, Vandenkoonhuyse et al. (2002, Evolution: Extensive Fungal Diversity in Plant Roots, Science, 295:2051-2051) used DNA sequence analysis to identify 49 species of fungi from the roots of a single grass plant, *Arrhenatherum elatius*. An even more complex community, consisting of 82 endophytic isolates, has been described in western white pine (Ganley et al., 2004, A community of unknown, endophytic fungi in western white pine, Proceedings of the National Academy of Sciences, 101: 10107-10112). The majority of these microbes appear to be neither parasites nor simple decomposers (Ganley et al., ibid), and many exist symbiotically within host plants. Concrete demonstrations of microbial abilities to enhance plant growth by facilitating nutrient and water uptake (Hildebrandt et al., 2002, Expression of nitrate transporter genes in tomato colonized by an arbuscular mycorrhizal fungus, Physiologia Plantarum, 115:125), increasing biomass production, and modifying expression of chemicals involved in plant defense [Bultman and Bell, 2003, Interaction between fungal endophytes and environmental stressors influences plant resistance to insects, Oikos, 103:182-190; Mucciarelli et al., 2003, In vitro and in vivo peppermint (*Mentha piperita*) growth promotion by nonmycorrhizal fungal colonization, New Phytologist, 158:579-591] all suggest that microscale communities have significant potential to influence vegetative communities.

Some aspects of inoculating plants with symbiotic fungi are commonly practiced. For example, many crops are inoculated with mycorrhizal fungi that improve nutrient uptake and water use efficiency. Some legumes are regularly inoculated with nitrogen fixing bacteria to improve performance. Inoculation with fungal endophytes has also shown promise to protect plants from pathogens (Arnold et al., 2003, Fungal endophytes limit pathogen damage in a tropical tree, PNAS, 100:15649-15654).

Recently, Redman et al. (2002, Thermotolerance Generated by Plant/Fungal Symbiosis, Science, 298:1581) disclosed the isolation of a novel fungal endophyte, a *Curvularia* sp., from *Dichanthelium lanuginosum* plants collected from geothermal soils. This isolated fungal endophyte was then inoculated onto endophyte-free *D. lanuginosum* plants. The endophyte inoculated plants exhibited substantially greater heat tolerance than endophyte-free plants of the same species. In all of these cases, endophytes were first isolated from their native host prior to transfer to the recipient plant.

SUMMARY OF THE INVENTION

We have now discovered a process for producing a novel plant material which comprises a first plant species or a part thereof having stably and heritably integrated therein one or more endophytic fungi which are derived from a second, plant species which may be the same as or different from the first plant species. Moreover, this first plant species is not a host plant for the endophytic fungi in nature (i.e., the endophytic fungi are not normally associated with the first plant species in nature). These resultant first plant species containing the endophytic fungi exhibit one or more of the following traits substantially increased vigor, altered morphology, higher yields, biochemical changes and increased reproductive potential compared to non-treated controls.

The process for transferring the above-mentioned endophytic fungi includes the steps of:
a. providing a plant or plant material of a first plant species, and
b. placing the plant or plant material of the first plant species adjacent to callus or surface disinfested tissue generated from a second, different plant species. The plant or plant material of the first species is also preferably surface disinfested. This contacting is for a period of time and under conditions effective to allow one or more endophytic fungi present in the second plant species to transfer therefrom to the first plant species and become stably integrated therein.

The resultant first plant species, having integrated therein the endophytic fungi from the second plant species, may then be recovered for subsequent growth or other use. As an alternative to placing the plant or plant material of the first plant species adjacent to callus or surface disinfested tissue generated from a second, different plant species, extracts of the second plant species containing viable endophytes can be prepared and injected directly into the tissues of the plant or plant material of the first plant species.

In accordance with this discovery, it is an object of this invention to provide plants or parts thereof containing stably and heritably integrated therein, endophytic fungi from a second, different plant species.

It is another object of this invention to provide plants or parts thereof which have stably and heritably integrated therein endophytic fungi which are not associated therewith in nature.

It is also an object of this invention to provide a process for producing plants or parts thereof which have stably and heritably integrated therein endophytic fungi which are not associated therewith in nature.

Yet another object of this invention is to provide plants or parts thereof which exhibit substantially increased vigor, altered morphology, higher yields, and increased reproductive potential.

Still another object of this invention is to provide plants or parts thereof which exhibit substantially increased vigor, altered morphology, higher yields, altered biochemistry, and increased reproductive potential without alteration of the plant's genome.

A further object of this invention is to provide a process for transferring endophytic fungi from one plant to another which does not require isolation of the fungi from their native host prior to transfer to the recipient plant.

BRIEF DESCRIPTION OF THE FIGURES

FIGS. 1(*a*) and (*b*) show dual stained plant tissue revealing fungi scattered throughout surfaces of epidermal tissue (a) and clustered around the guard cells of a *B. eriopoda* stomatal complex (b). FIGS. 1(*c*) and (*d*) show electron micrographs of a biofilm encasing emerging roots and shoots of regenerated plants (c), and teleospores characteristic of rust fungi (d).

FIG. 2*b* shows germinating seedlings of *S. cryptandrus* (sand dropseed, left) and *S. cryptandrus* inoculated with endophyte containing callus from *B. eriopoda* (black grama, right).

FIG. 10 shows phyllogenetic analysis of rDNA obtained from *Bouteloua eriopoda* regenerated plants and associated endophytes and illustrates the diversity of heritable endophytes present in a single species. In the cladogram, arrows identify sequences derived from *B. eriopoda* regenerated plants and associated endophytes. These sequences represent not only the *B. eriopoda* DNA but also fungi four or more phyla.

DETAILED DESCRIPTION OF THE INVENTION

Figure 1:
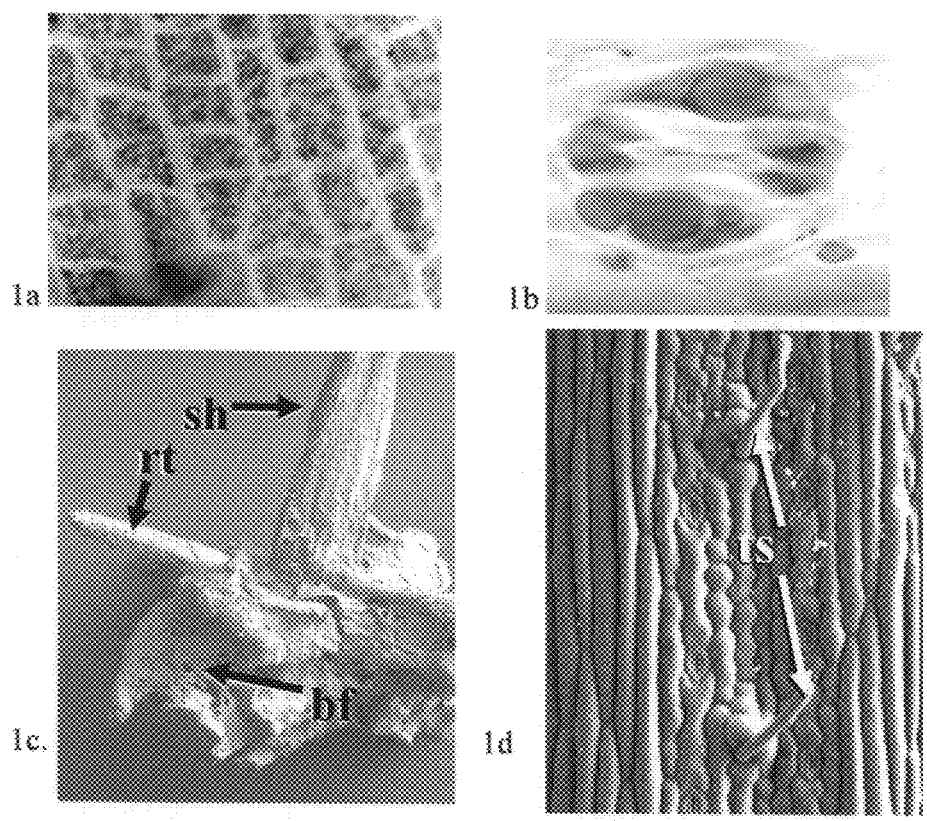
FIG. 1 shows fungi detected in all major tissues and cell types of aseptically grown *B. eriopoda* as described in Example 1.
Figure 2:
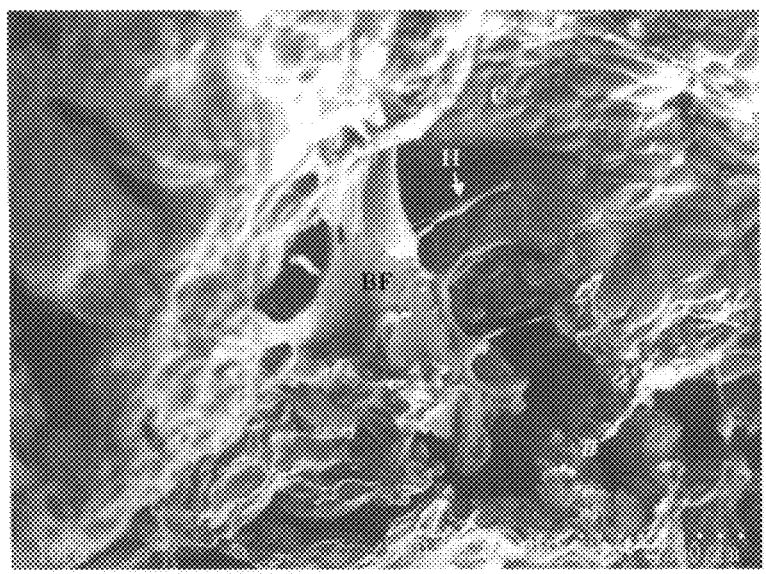
FIG. 2 shows an SEM image of axenically cultured black grama callus (*B. eriopoda*) encapsulated with a fungal biofilm (BF). Fungal hyphae (H) are enmeshed within the biofilm.

In producing the plants of this invention we have transferred into a plant, one or more endophytic fungi, which may also be symbiotic, and which are not normally associated with the plant. Moreover, while these fungi become stably and heritably integrated into the plant, the genome of the plant is itself not changed. We have discovered that these endophytic fungi are at least maternally transferred to successive generations, and remain associated with the plant even if the seed thereof is surface disinfected prior to growth. Plants having these non-native fungal endophytes integrated therein exhibit a number of improved properties, including one or more of increased vigor, allowing for growth under harsh environmental conditions such as reduced water, poor nutrients (i.e., the water and nutrient use efficiency of the plants may be increased), and high temperatures, increased chlorophyll content and phosphorous uptake, altered morphology, including altered or more extensive root systems, higher yields, including plant biomass, biochemical changes, including, for example, production of fatty acids, pigments, and organic acids not present in the untreated plant or production in higher amounts, and increased reproductive potential, including earlier and larger fruits and seed production. It is also envisioned that integration of these non-native fungal endophytes may provide increased resistance to disease and harmful pests.

Surprisingly, we have discovered that many of the endophytic fungi associated with their natural host plants cannot be isolated and propagated in vitro (i.e., cultured) by conventional culture techniques using known mycology media (e.g., potato dextrose agar, corn meal agar, MS agar, Luria Bertani or LB agar, or trypticase soy agar). For the purposes of this invention, fungi "associated with" their natural host plant (or "normally associated with" a plant species) refers to the presence of the fungi within the tissue of the plant in the plant's natural environment, such that the fungi are stably structurally integrated within the plant and are heritably transmitted through seed thereof to successive generations. Thus, techniques such as those described by Redman et al. (2002, ibid) or Johnson-Cicalese (2000, Cross species inoculation of chewings and strong creeping red fescues with fungal endophytes, Crop Science, 40:1485-1489) wherein fungal endophytes are first isolated from their natural host plant and cultivated in vitro, and the isolated fungi are then used to inoculate another plant, are not required, and for many endophytes, are not suitable for use herein. However, we have found that despite the inability of many fungal endophytes to be isolated and grown in vitro, these fungi can be transferred by use of the process of this invention. In accordance with this invention, transfer of the endophytic fungi to a non-host first plant species is effected by placing plant or plant material of the recipient and donor plant species adjacent to one another in a manner that reduces or eliminates competition from external microbes, particularly the biofilm enveloping the external surfaces of the plants, which may otherwise impede recipient plant colonization by donor plant endophytes.

In accordance with a first preferred embodiment, the fungal endophytes may be transferred by use of undifferentiated cell masses (i.e., callus) of a second plant species which serves as the source material for the fungi. In accordance with this process, either a viable plant or plant material of the first plant species is placed adjacent to (i.e., contacting or in close proximity to such as within several millimeters), preferably in contact with, callus generated from the second, different plant species. The recipient plant or plant material and the callus are maintained in this relative placement or contact for a period of time and under conditions effective to allow one or more of the endophytic fungi present in the callus of the second plant species to transfer therefrom to the first plant species and become stably integrated therein. The particular conditions chosen are generally not critical, but should be conducive to growth of the first plant species, the donor, second plant species or callus, and the endophytes. Transfer of the fungal endophytes to the plant or plant material of the recipient, first plant species from the callus is also enhanced by surface disinfestion of the first species plant or plant material prior to its placement adjacent to the callus. Surface disinfestion (which may be referred to as surface disinfection) may be conducted using conventional surface disinfection or sterilization techniques which are effective for removing the microbial biofilm enveloping the external surfaces of the plant, at least at the location on the surface adjacent to the donor callus, without damaging the plant itself. Without being limited thereto, preferred surface disinfestion techniques include treatment with chemical germicidal agents such as ethanol, isopropyl alcohol, sodium hypochlorite, hydrogen peroxidate or hydrogen dioxide. The callus of the second plant species may be produced by conventional techniques. Callus which is up to 2 years old has been used successfully herein. The callus may be in whole, ground, or liquified form. We have discovered that the endophytic fungi begin transferring to the plant or plant material of the first plant species almost immediately upon contact with the callus. The optimal time period for the contact will vary with the plant or plant material selected for use as the first plant species. However, after 5 days the fungi typically permeate the entire intercellular space of the seedling and become integrated with host cell membranes, and the treated first plant species may be recovered for subsequent use. Moreover, because the endophytic fungi become integrated with all meristematic cells of the first plant species, they become a heritable component and are transferred through the seed to successive generations.

In a particularly preferred embodiment, the transfer of the endophytic fungi from the callus of the second plant species is effected by contact with a seed, germinated seed, or seedling of the first plant species in tissue culture. This culture may utilize any conventional culture media suitable for plant cell growth, such as hormone-free Murashige and Skoog (MS) agar, commercial potting soil, or vermiculite. The plant material of the first plant species and callus of the second plant species are also preferably contacted under aseptic culture conditions to prevent growth of microbial contaminants which may create physical barriers preventing or inhibiting colonization of the recipient plant by donor endophytes.

In an alternative embodiment for transfer of the fungal endophytes without the use of callus, we have discovered that the endophytes may be transferred by substituting for the callus, plant or plant material of the second, donor plant species which has been surface disinfested or lichen. Thus, the process for transferring the above-mentioned endophytic fungi includes the steps of:
 a. providing surface disinfested plant or plant material of the first plant, and
 b. placing the plant or plant material of the first plant adjacent to surface disinfested tissue from the second plant or lichen.

As with the use of callus, the donor and recipient plants or plant material or lichen are maintained adjacent to one another for a period of time and under conditions effective to allow one or more endophytic fungi present in the second plant to transfer therefrom to the first plant and become stably integrated therein. A variety of plant tissues are suitable for use as the donor plant material, and include but are not limited to leaves, roots or stems, while the recipient plant material is preferably a seed, germinated seed, or seedling, with seedlings being particularly preferred. As an alternative to plants, it is also envisioned that lichens may be used as a donor species for the endophytic fungi. The donor plant material may be collected from plants in aseptic or natural or agricultural settings.

Fungal endophytes may also be transferred by injection of donor plant or lichen extracts containing viable endophytes directly into the tissue of the recipient plant or plant material in accordance with another alternative embodiment. Use of this technique is particularly suited for transfer of endophytes to relatively slow growing recipient plant species such as trees. Donor plant extract containing endophytes for injection may be prepared using a modification of the process described by Atsatt for extraction of plant mycosomes (Atsatt P. R., Fungus propagules in plastids: the mycosome hypothesis, International Microbiology, 617, 2003, the contents of which are incorporated by reference herein). In this embodiment, plant tissue, plant material or callus of the first, donor plant species or lichen is ground in buffer to form an injectable endophyte cell suspension. The tissue, material, callus, or lichen is preferably ground sufficiently to disrupt the cell wall structures of at least some plant cells to facilitate the release of fungal endophytes into the buffer. The ground material is sieved to remove large particulate and fibrous material, and sieved through an approximately 0.4µ filter to produce a suspension sufficiently fine to be readily injectable. The filtrate may be collected and optionally but preferably concentrated, such as by centrifugation. The concentrated filtrate containing the fungal endophytes may then be directly injected into the recipient plant or plant material. The site of injection may be varied, although the stem or nodes are generally preferred. Injection may be conducted using conventional syringes, such as syringes fitted with a 22 gauge needle. The amount of donor plant material or lichen necessary for effective transfer of the fungal endophytes may vary with the particular species and size of the recipient plant, and may be determined by routine experimentation. However, without being limited thereto, for practical purposes, typical volumes of injectable concentrate injected into the recipient plant will be between about 0.5 to about 1 ml, with each ml of injectable concentrate containing approximately 1 g of fresh donor plant or lichen tissue. A variety of buffers are suitable for use to prepare the donor plant or lichen extract, and include but are not limited to aqueous buffers with controlled ionic strengths, such as phosphate buffered saline with a pH of between about 5.5 to about 7.5.

As noted above, the fungal endophytes which are transferred to the first plant species are derived, from a second, different plant species which may be the same as or different from the first plant species. For the purpose of this invention, "derived from" is not limited solely to the direct transfer of the fungal endophytes from the second to the first plant species, but also encompasses transferring the fungi through an intermediate plant. In other words, once the fungal endophytes have been transferred to a plant or plant material of the first plant species, the skilled practitioner will recognize that a specimen of that treated plant or plant material (or its progeny) may then be used as a host plant to generate callus to transfer the fungal endophytes to an untreated plant or plant material of the same or different first plant species. Thus, in an alternative embodiment, it is understood that the fungal endophytes may be transferred to the first plant species by a process wherein an untreated first plant species or plant material therefrom are placed adjacent to callus generated from a plant or part thereof of the first plant species (or its progeny) which was previously treated to incorporate the fungal endophytes from a second, different plant species. This plant or plant material of the first plant species and the callus may then be incubated in the same manners described hereinabove to allow transfer of the fungal endophytes.

In the accordance with this invention, endophytic fungi can be transferred not only to target plants of different species, but to virtually any different genus as well as plants of different ecosystems. Thus, a wide range of second plant species are suitable for use as target plants herein, although desert grasses and commercially valuable plants and crops are preferred. Without being limited thereto, it is envisioned that examples of preferred plants for incorporation of the endophytic fungi include grasses, grains, forage, berries, fruit trees, nut trees, forest trees, vegetables, ornamental flowers, shrubs, herbs including medicinal herbs such as chinese wolfberry, particularly barley, canola, maize, oats, rice, safflower, sorghum, sunflower, wheat, alfalfa, forage legumes, strawberry, cranberry, blueberry, raspberry, blackberry, apple, peach, pear, plum, and cherry trees, pecan and almond trees, sweetgum, aspen, loblolly pine, cottonwood, poplar, maple, eucalyptus, and radiata pine trees, asparagus, broccoli, cauliflower, cabbage, green beans, dried beans, lettuce, mint, lentils, onion, peas, peppers, potato, tomato, carrots, grapes, watermelon, cantaloupe, cucumbers, cotton, peanuts, sugar cane, soybeans, chiles, sugar beets, turf grasses, *Arabidopsis*, tobacco, *Yerba mansa*, lavender, papaya, mango, coffee, cacao, and desert grasses and shrubs.

A wide range of second plant species may also be used to generate the callus used as the source of the endophytic fungi. While we have found that fungal endophytes are structurally integrated throughout a number of desert plants in nature and remain associated therewith even when the plants are regenerated in vitro from surface disinfected embryonic cells under aseptic tissue culture, we believe that the structural integration of such fungal endophytes throughout the plant is not unique to these desert plants. Thus, while the use of desert plants as the second plant species is preferred, it is envisioned that virtually any plant may be used. In general, the selection of the actual second plant species used may be made in accordance with the desired characteristics which are to be conferred to the target first plant species. For example, selection of desert shrubs and grasses may confer increased water and nutrient use efficiency and heat tolerance, while selection of other second plant species may be used to increase the production of desired plant metabolites and natural products for subsequent recovery and commercial use. Halophytes may provide endophytes that confer salt tolerance to non-native plants, and plants that are unaffected by a particular pathogen may provide endophytes that confer disease resistance. In the preferred embodiment using desert plants, second plant species for use herein include but are not limited to desert grasses and shrubs, particularly black grama (*Bouteloua eriopoda*, (Torr.) Torr.), sand dropseed (*Sporobolus cryptandrus* (Torr.), alkali sacaton (*Sporobolus airoides* Torr.), fourwing saltbush (*Atriplex canescens*, Pursh Nutt.), Griffith's saltbush (*Atriplex griffithsii* Standl.), glassworts (*Salicornia* species), and other plants from the family Chenopodiacea, in addition to mesquite (*Prosopis* species), creosote bush (*Larrea* species), jimson weed (*Datura inoxia*

Mill.), *Yucca elata*, broom snakeweed (*Gutierrezia* species), *Opuntia* species, *Prosopis* L., and *Prosopis glandulosa*. Other preferred, non-desert plants for use as donor tissue or callus include rice (*Oryza sativa*), *Arabidopsis thaliana*, *Tripsacum dactyloides*, plains bristlegrass (*Setaria vulpiseta*), and *Cucurbita foetidissima*. It is also envisioned that lichen may be used as donor tissue.

The following examples are intended only to further illustrate the invention and are not intended to limit the scope of the invention which is defined by the claims.

Example 1

In this study we transferred endophytic fungi inhabiting two perennial grasses, *Bouteloua eriopoda* (black grama) and *Sporobolus cryptandrus* (sand dropseed), and one shrub, *Atriplex canescens* (fourwing saltbush), to a variety of non-host desert plant species. Dramatic, whole-plant differences in morphology and biomass between treated and untreated plants were observed. In at least two cases, endophyte transfer at the cellular level produced larger plants with greater reproductive potential than the untransformed counterparts.

Methods and Materials

Plant Material

Seeds and tissues from *B. eriopoda*, and *Atriplex canescens* were collected from native populations on the USDA-ARS Jornada Experimental Range near Las Cruces, N. Mex. Seeds for *S. cryptandrus* were purchased from Plants of the Southwest in Santa Fe, N. Mex. *B. eriopoda* callus was induced by germinating surface disinfested seeds under aseptic conditions. Embryonic shoots were excised and cultured on Murashige and Skoog (MS) agar (Murashige and Skoog, 1962, A revised medium for rapid growth and bioassays with tobacco tissue cultures, Physiologia Plantarum, 15:473-497) to produce callus. Callus cultures were maintained on MS agar containing 4.52 μM Dicamba (6-dichloro-o-anisic acid), at 25° C. with an 18 h photoperiod (151 μmol m$^{-2}$ s$^{-1}$). The callus was transferred to hormone free MS agar for multiplication prior to inoculation of foreign host tissue.

Aseptic shoot cultures of *A. canescens* were established as described above, then transferred to a callus initiation media (MS basal salts supplemented with 3.5 μM 4-Amino-3,5,6-tricloropicolinicacid (Picloram) and 8.87 μM 6-Benzylaminopurine (BAP). Callus was transferred to hormone-free MS agar prior to seedling inoculation. *A. canescens* cultures were incubated at 28±1° C. under continuous fluorescent light (14-18 μmol m$^{-2}$*s$^{-1}$).

Isolation of Endophytic Fungi

Roots were washed in tap water to remove soil, then surface-disinfested by soaking in 70% ethanol for 7 min, followed by 3.9% sodium hypochlorite (75% CLOROX) for 30 min. Alternatively, some *A. canescens* roots were soaked in 95% ethanol for 1 min followed by 2.6% sodium hypochlorite (50% Chlorox™) Disinfested root sections or regenerated shoots were cultured on potato dextrose agar (PDA) and incubated in a controlled environment. Fungal hyphae emerging from the nodes or cross-sections of root segments were removed and transferred to Potato Dextrose Agar.

One fungal strain isolated from *B. eriopoda* was identified morphologically as *Aspergillus ustus* by Dr. Marin Klich, USDA-REE-ARS-MA-SSRC-F&FAR. A morphologically identical endophyte was also isolated from roots of *A. canescens*.

A second species isolated from *B. eriopoda* roots was tentatively identified by Dr. M. Catherine Aime, USDA, ARS Systematic Botany and Mycology Lab, Beltsville, Md., as a *Moniliophthora* species, based on sequence analysis of ribosomal DNA.

*Penicillium olsonii*, and *Bipolaris spicifera*, isolated from *A. canescens* in vitro, and *Engyodontium album*, isolated from in vitro *B. eriopoda*, were identified by sequence analysis of the internal transcribed spacer region (ITS1-5.8S-ITS2 rDNA) of ribosomal DNA. These analyses were performed by the Plant Pathogen Identification Lab at North Carolina State University. A putative Urediniomycete was identified by observation of teliospores in light and electron micrographs of *B. eriopoda* leaf tissue. To confirm identity of this species, which cannot be cultured independently of the host plant, total DNA was extracted from plant tissues produced in vitro using MoBio Ultraclean™ Plant DNA Kits. DNA was amplified by polymerase chain reaction using the primers: Puc_rDNA_F, 5'GCATTCCCAAACAACTCGAC3' (SEQUENCE ID No. 1) and Puc_rDNA_R, 5'CCTGTTTGAGTGTCATGAAACC3' (SEQUENCE ID No. 2) with Taq PCR Master Mix (Qiagen, Inc.) at an annealing temperature of 60° C. The amplified product was cloned into pCR 2.1 plasmids using Invitrogen TA CLONING KIT. Individual clones were sequenced using universal M13 forward and reverse primers and BigDye Terminator v3.1 Cycle Sequencing Kit (Applied Biosystems) in conjunction with an Applied Biosystems 3100 Genetic Analyzer. To identify other potential endophytes, either AU2 and AU4 (Vandenkoornhuyse et al., ibid) or ITS1 and ITS4 (White et al., 1990, Amplification and direct sequencing of fungal ribosomal RNA genes for phylogenetics. In: Innis et al., (Eds), PCR Protocols: A Guide to Methods and Applications, Academic Press, Inc., New York, pp. 315-322) primer pairs were used to amplify DNA from regenerated shoot cultures of *B. eriopoda* and *A. canescens* as described above. An annealing temperature of 48° C. was used for these amplifications. PCR products were cloned into pCR2.1 plasmids.

Microscopic Examination of Plant Tissue

Tissues from either field collected or in vitro plant material were stained as described by Barrow and Aaltonen [2004, A staining method for systemic endophytic fungi in plants, In: Lartey and Caesar, (Eds.), Emerging Concepts in Plant Health Management, Research Signposts, Kerala, India (In press)]. Tissues were mounted on microscope slides and examined with a Zeiss Axiophot microscope using both conventional and DIC optics at 1000× magnification. Electron microscopy was performed by Soumitra Ghoshroy at the Electron Microscopy Laboratory, New Mexico State University, Las Cruces, N. Mex. 88003.

Inoculation of Foreign Hosts

Callus cultures of *B. eriopoda*, *A. canescens* or *S. cryptandrus* were incubated with surface disinfested, germinating seed and cultivated aseptically in MS agar. Specifically, seeds of *B. eriopoda* were incubated with callus of either *A. canescens* or *S. cryptandrus*. Seeds of *S. cryptandrus* were incubated with callus of *B. eriopoda*.

Results

Dual staining with Trypan Blue, selective for fungal chitin, and Sudan IV, specific for fungal-associated lipid bodies, revealed the presence of fungi associated with every cell type examined. In addition to the long and short epidermal cells (FIG. 1a) and stomatal complexes (FIG. 1b), mesophyll, vascular bundles and somatic embryos (not shown) have all stained positive for fungi. Using transmission electron microscopy, vacuolated fungal hyphae were observed between plant cell walls and membranes, even appearing to encircle the chloroplasts. Using scanning electron microscopy, fungal networks and biofilms appear to cover the surface of *B. eriopoda* leaf tissue (FIG. 1*c*), and teliospores are evident (FIG. 1*d*). Similar images have been obtained from both aseptic and field collected specimens of *B. eriopoda* and *A. canescens*.

Fungi isolated and identified from aseptically cultured *A. canescens* include *Penicillium olsonii, Bipolaris spicifera*, and *Aspergillus ustus*. From aseptically cultured *B. eriopoda*, we have isolated and identified a novel species of *Aspergillus ustus, Engyodontium album* and an endophyte tentatively identified as belonging to the genus *Moniliophthora*. In addition to the species listed above, the teliospores present on *B. eriopoda* suggest the presence of a fungus similar in morphology to rust-causing fungi such as *Puccinia* (FIG. 1*d*). PCR primers targeting *Puccinia* internal spacer regions do produce a fragment of the predicted size when used to amplify total DNA from plant cultures. However, no disease symptoms are present in the host plant. Finally, a cloned PCR fragment amplified from *B. eriopoda* callus DNA is homologous to an unidentified ascomycete (Genbank accession number AY559361), and similar to several species of *Cercospora*. To summarize, we found evidence of at least six fungal species residing within *B. eriopoda*, and at least three species in *A. canescens* callus and regenerated plants.

Figure 3:
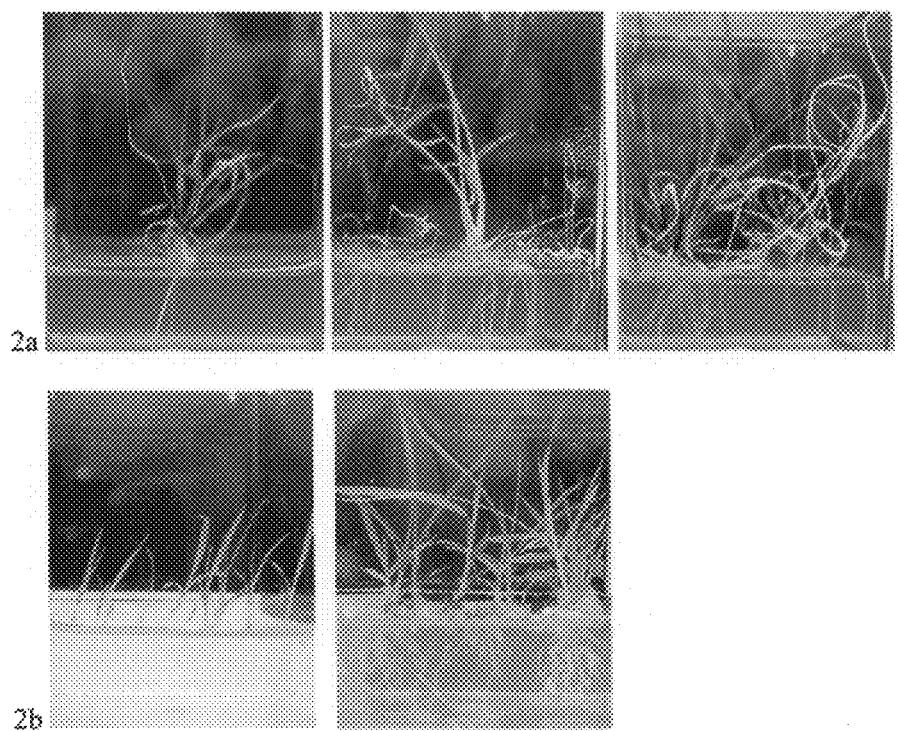
FIG. 3 shows plants treated in Example 1. The differences in root and shoot biomass are readily observed between germinating seedlings of *B. eriopoda* (2*a*, left) and *B. eriopoda* inoculated with callus from *S. cryptandrus* (2*a*, middle), and *B. eriopoda* inoculated with callus from *A. canescens* (2*a*, right).

To examine host specificity of endophytes, surface sterilized seeds from *B. eriopoda* were incubated in the presence of callus tissue from *A. canescens*. Ninety percent of the inoculated seedlings displayed greater total biomass (FIG. 3*a*, right) than the uninoculated control plants (FIG. 3*a*, left). Root branching and tiller production were both greater in inoculated *B. eriopoda*, suggesting fungal induction of morphological changes in the host plant. When *S. cryptandrus* was inoculated with *B. eriopoda*, similar results were observed (FIG. 3*b*). Out of 30 inoculated seedlings, 30 plants survived and produced greater shoot and root biomass than uninoculated controls. Results were less straight-forward when *B. eriopoda* seedlings were inoculated with *S. cryptandrus* callus (FIG. 3*c*). In this situation, out of 63 inoculated seedlings, only 12 survived. Of these 12 plants, four produced greater root and shoot biomass than the uninoculated controls.

Discussion

The intricacy of fungal networks observed within individual cells and tissues of *B. eriopoda* and *A. canescens* in vitro suggests that few, if any, physiological processes within these plants are not influenced by surrounding fungi. Demonstrations of the unique roles played by each member of this plant-fungus community have been hindered by difficulty in isolating obligate fungal species which cannot grow apart from host plants. Equally difficult has been the isolation of endophyte-free plant cells, since endophytes are present even at single cell and embryonic stages. The induction of fruiting bodies; crucial for morphological identification of fungi, does not always occur within plant tissues, especially under the arid conditions found in natural settings. It is notable that all of the fungal species described herein were isolated from plants grown in vitro, either from callus tissue or regenerated plants. Thus even if fungal endophytes serve tissue specific functions within a developed plant, the species identified in this study are all associated with undifferentiated plant tissues (callus) at the cellular level. Equally important, these species have also been detected in field samples collected from a number of sites on the Jornada Experimental Range. This assures us that the endophytic associations we are observing are natural components of the plant species examined.

The teliospores illustrated in FIG. 1*d* are characteristic of rusts. Historically, *B. eriopoda* has been described as a host plant for *Puccinia cacabata*, the causative agent for Southwest Cotton Rust. *Puccinia* species are generally obligate, and cannot be cultured independently of the host. To determine whether the teliospores were being produced by a rust, PCR primers were designed by aligning internal spacer sequences of rDNA from *Puccinia* sequences in Genbank, *B. eriopoda, A. ustus, Moniliophthora* sp., and *E. album*, using the ClustalW algorithm (Higgins et al., 1994, CLUSTAL W: improving the sensitivity of progressive multiple sequence alignment through sequence weighting, position-specific gap penalties and weight matrix choice, Nucleic Acids Research, 22:4673-4680). Regions of the alignment that were conserved only among *Puccinia* were selected for forward and reverse PCR primers. The BLAST Search for short nearly exact matches (McGinnis and Madden, 2004, BLAST: at the core of a powerful and diverse set of sequence analysis tools, Nucleic Acids Research 32:W20-W25), used to test primer specificity, invariably returned *Puccina* or other *Uredomycetes* as matches, and the primers amplified a product of the predicted size when used to amplify DNA from *B. eriopoda*. However, the amplified sequence exhibited weak homogeneity when aligned with *Uredomycetes* in Genbank. Failure to align with previously described species suggests that either the teleospore producing fungus belongs to a novel species, or that the amplified PCR product came from another endophyte present in *B. eriopoda*.

Our observation of fungal networks from both monocots and dicots in vitro, combined with observation of similar fungal structures, including teliospores, in tissues collected from more than 35 species (not shown) indicate these relationships are highly conserved. It is generally assumed that highly conserved features serve crucial functions. We suggest that the biofilms enveloping external plant surfaces shield plants from the harsh environments encountered in arid rangelands. The fungi observed in stomatal complexes may have a direct role in regulating evapotranspiration, while hyphae observed in colonized roots function not unlike traditional mycorrhizae, increasing the surface area available for uptake of nutrients, particularly phosphorus (Barrow and Osuna, 2002, Phosphorus solubilization and uptake by dark septate fungi in fourwing saltbush, *Atriplex canescens* (Pursh) Nutt., Journal of Arid Environments, 51:449-459).

The identification of five fungal endophytes associated with a single grass species in aseptic cell and tissue cultures has profound implications for plant ecologists, especially when coupled with the dramatic changes in plant morphology we observe when endophyte communities are changed. Of equal interest is the discovery of *A. ustus* behaving as an endophyte in both a grass and a shrub. We know that *A. ustus* assists with phosphorus uptake in *A. canescens* (Barrow and Osuna, 2002, ibid). This fungus can spread through the soil either vegetatively or with spores. If the same genotype can inhabit multiple plant species, this microbe may provide an unexplored source of connectivity between plant species in a single community. Clearly, analysis of microbial communities associated with vegetation would improve our understanding of the existing variability among plant communities.

Such analysis was once considered an insurmountable task, but increasingly available DNA sequence information coupled with modern high-throughput techniques in molecular biology make the task of monitoring changes in microbial communities feasible. A microarray containing well defined ribosomal marker sequences collected from key plant and soil types could provide invaluable information regarding site conditions pre- and post-disturbance. As data accumulate relating site conditions to microbial communities, changes in species composition may be useful for predicting changes in plant communities.

Perhaps the most significant aspect of the results described herein concerns the startling changes in plant morphology and biomass observed following inoculation of species with endophyte-containing callus. The enhanced growth of *S. cryptandrus* and *B. eriopoda* following inoculation with endophyte containing callus suggest endophyte manipulation may provide a powerful tool for developing plant cultivars capable of thriving in harsh environments. This observation parallels the findings of Redman et al. (2002, ibid), whose tomatoes survived constant temperatures of 50° C. following inoculation with thermotolerant fungi.

Example 2

The experiments in Example 1 were expanded to transfer endophytic fungi from perennial desert grasses and shrubs to a variety of non-host commercial crops, including tomato, chile, wheat, onion, sorghum, cotton, carrot, and tobacco.

Figure 4:
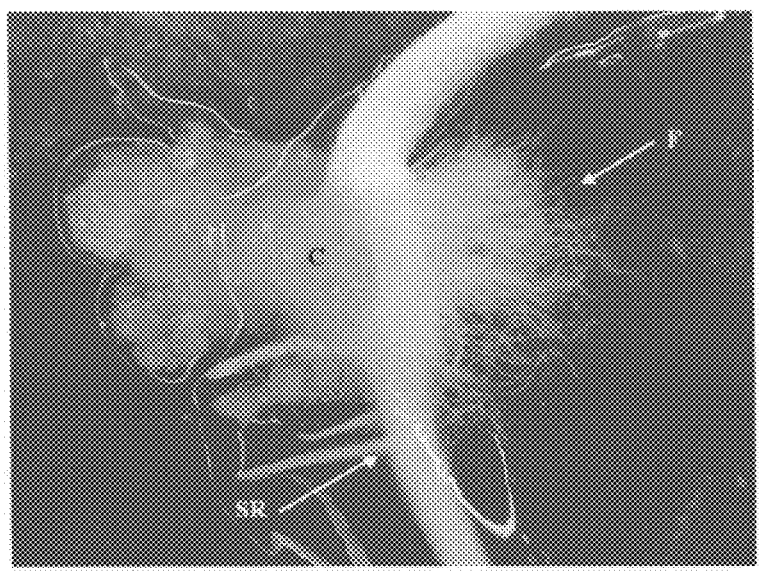
FIG. 4 shows a tomato seedling is placed in contact with black grama callus [C] integrated with symbiotic fungi as described in Example 2. Fungi [F] appear to rapidly transfer from the callus and systemically permeates the seedling. Note, that the fungi are associated only with the callus and seedling. It does not grow on the carbon-mineral rich culture medium.

Seeds of each of the above-mentioned non-host plants were surface disinfected, and germinating seedlings were placed in contact with black grama callus as described in Example 1. The symbiotic fungi from the black grama callus rapidly transferred from the callus to the non-host seedlings (FIG. 4), and within five days, the fungi had permeated the entire intercellular space of the seedlings and became integrated with host cell membranes.

Figure 5:
FIG. 5 shows chile plants produced in Example 2. Fungus from black grama transferred to the Chile plant (var. NM 64) on the left has greater shoot and root biomass, earlier and larger fruits, approximately twice the chlorophyll content compared to the control plant without fungi on the right. Plants were grown with equal soil volume, nutrient and water content. Fungi induce substantial morphological changes with enhanced nutrient and water use efficiency.
Figure 6:
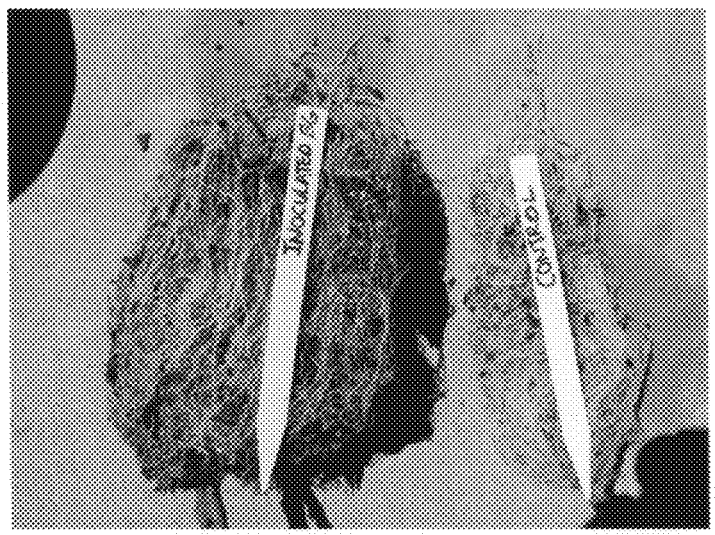
FIG. 6 shows the roots of tomato plants produced in Example 2. Roots of tomato plants with transferred black grama fungi have approximately 5 times the biomass and greater branching than roots of the control plant without the fungus.

The resultant plants containing the integrated endophytic fungi from the black grama were recovered and compared to nor-treated controls. The transfer of the fungi from native black grama grass to tomato, chile, wheat, onion and tobacco and induced phenomenal responses in vigor, morphology and reproductive potential. For example, chile plants symbiotic with black grama fungi were more vigorous, with greater root and shoot biomass (FIG. 5) and produced more, earlier and larger fruits compared to non-symbiotic plants when grown with equal soil volume and quantities of water and nutrients. The effect of the transfer of the endophytic fungi on a common tomato variety of tomato plants is shown in FIG. 6. As shown therein, treated tomato plants exhibited a remarkable increase of root biomass generated that was five times greater than control tomato plants without the fungi (on the right).

Figure 7:
FIG. 7 shows tomato plants produced in Example 2. Second generation tomato plant, on the right, from a parent with transferred black grama fungus. Plant on the left, without the fungus, shows purple phosphorous deficiency symptoms. Plant tissues with black grama fungus have 0.44% P compared to 0.23% P in the control plant and 13.5 µg/ml extract of chlorophyll compared to 8.6 u/ml in the control plant.
Figure 8:
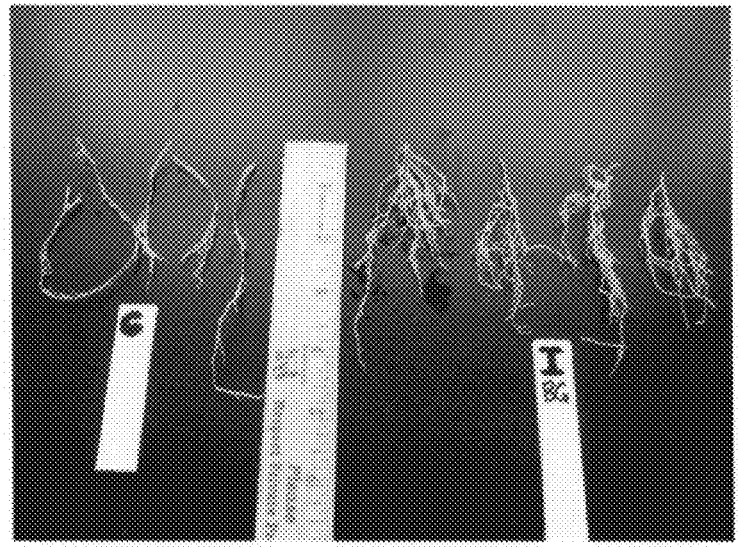
FIG. 8 shows the roots of tomato plants produced in Example 2. Comparison of roots of tomato plants without fungus, on the left, with roots of second generation plants with black grama fungus. Vertically transmitted fungi via seed are expressed as modifying root structure in the second generation.

Second generation tomato plants were then generated from the treated tomato plants to demonstrate heritability. Once integrated into the cell structure (i.e., bound to the cell membranes) symbiotic fungi became heritable units and were transferred to succeeding generations by seed. As shown in FIG. 7, tomato progeny symbiotic with black grama fungi on the right had 0.44% phosphorous in leaf tissue compared to non-symbiotic plant on the left that had 0.23% phosphorous, which also showed symptoms (purple coloring) of phosphorous deficiency. Symbiotic plants also had 13.5 µg/ml extract of chlorophyll compared to the non-symbiotic plant with 8.6 µg/ml extract. FIG. 8 shows the enhanced root modification in symbiotic progeny on the right compared to non-symbiotic progeny on the left demonstrating the heritability of these fungi. Second generation wheat plants were generated from the treated wheat plants and also exhibited increased vigor.

Example 3

The experiments in. Examples 1 and 2 were repeated to examine the biochemical effects of the transfer endophytic fungi from *Datura inoxia* to tomatoes. Tomato seeds were surface disinfected, and germinating seedlings were placed in contact with *Datura inoxia* callus and recovered as described in Example 1.

Figure 9:
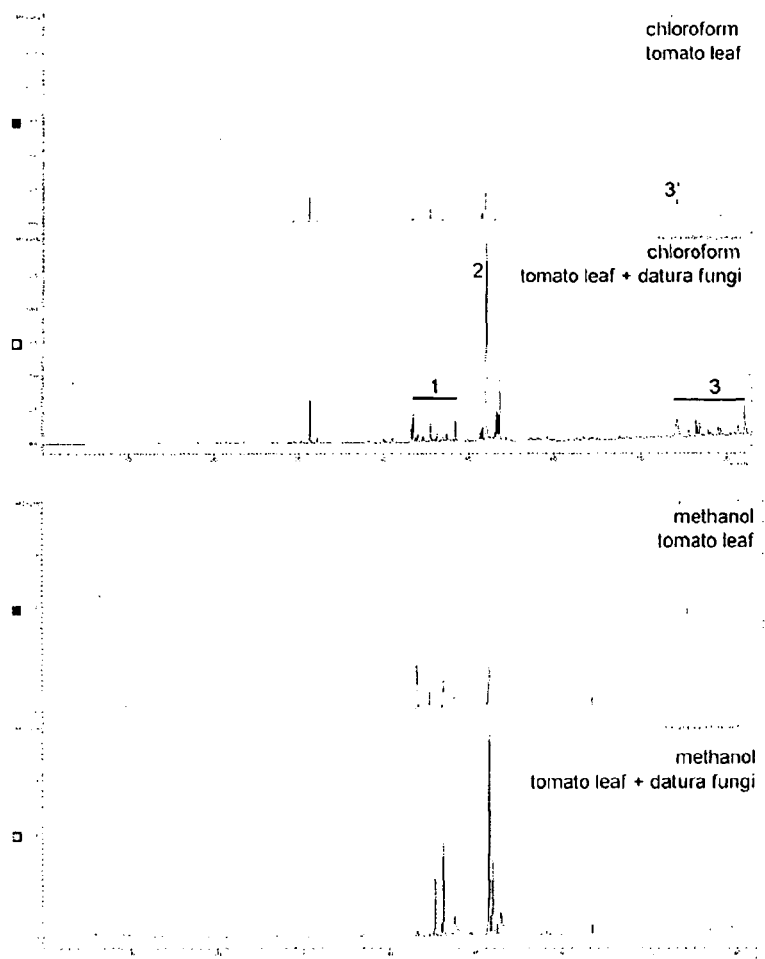
FIG. 9 shows the Relative Ion Counts (GC/MS) chromatograms of tomato leaf extracts from control plants or plants inoculated with endophytes from *Datura inoxia* as described in Example 3. Major peaks were identified based on mass spectra matches as follows: 1 fatty acids, 2 phytol, 3 carotenoids and steroids, and 3' lycoxanthin. These compounds are more abundant in the endophyte treated plant, suggesting that endophytes are responsible for the enhanced expression of the indicated primary metabolite.
Figure 10:
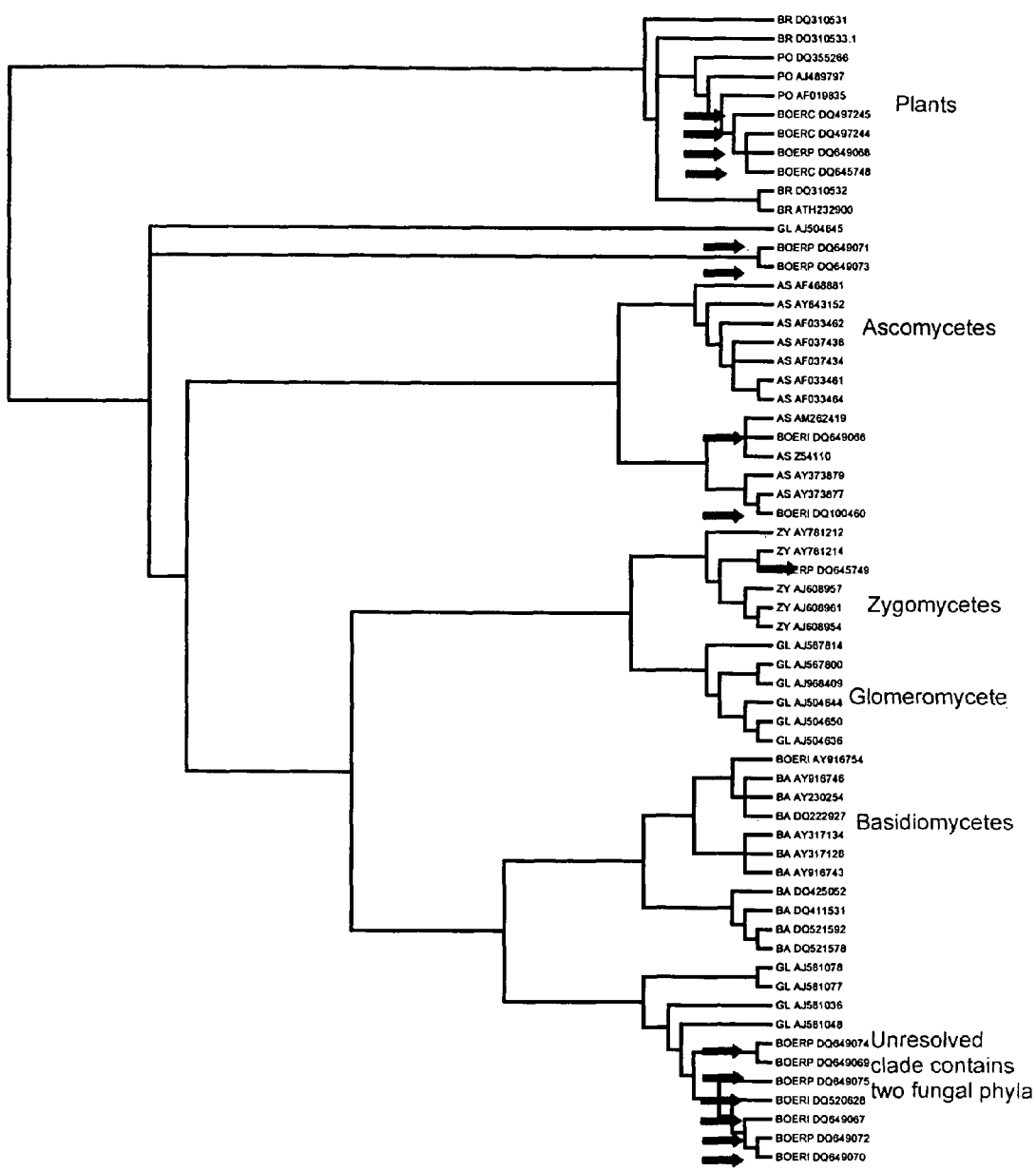
FIG. 10 illustrates the genetic diversity of fungi isolated in the Example.
Figure 11:
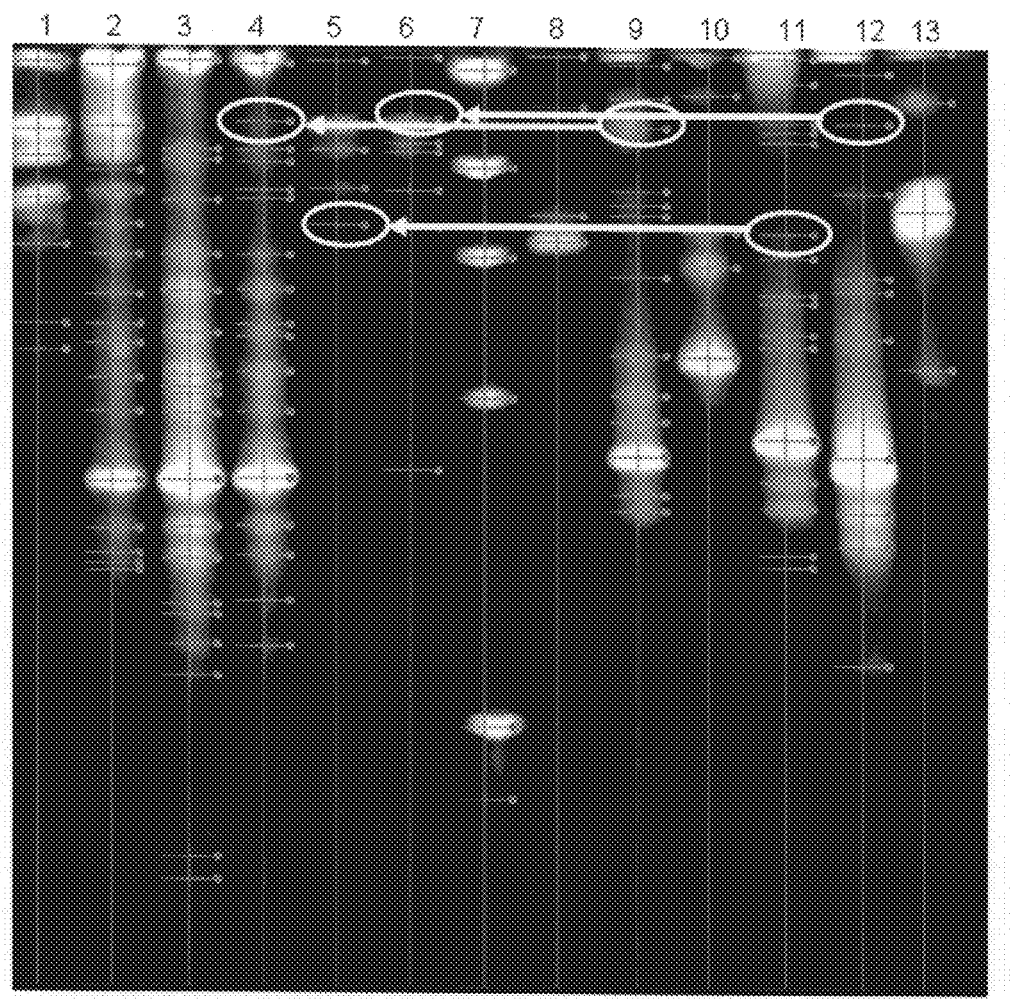
FIG. 11 shows the denaturing Gradient Gel Electrophoresis of ribosomal DNA gene fragments used to separate plant and endophyte DNA. Here we demonstrate that several bands are present in DNA isolated from in vitro cultures. Some of these sequences originate in the plant, others come from endophytes. By comparing banding patterns of DNA amplified from callus cultures (second plants), pretreated first plants, and posttreated first plants we can demonstrate that sequences representing endophyte DNA from the second plant can be observed in first plants after endophyte transfer as described above. In this figure, DGGE separation of PCR products from uninoculated tomato host plant (Lyes, Lane 1, left to right), inoculated host plants (Lanes 2-4), and callus cultures of native plants (Lanes 6-10), reveal movement of genetic material. Circles highlight bands from donor plant endophyte profiles that appear in recipient plants following exposure to donor callus. Some bands indicative of native endophytes in untreated recipient plants disappeared following treatment. The ability to eliminate competing endophytes from the first plant may have implications for treatment of plant diseases.
Figure 12:
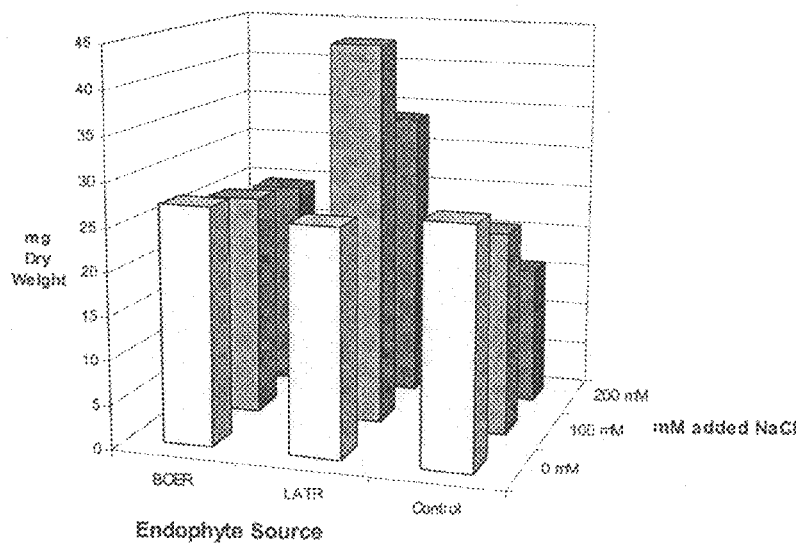
FIG. 12 shows the impact of endophytes on chile seedling biomass and salt tolerance. Endopohytes from *Bouteloua eriopoda* (BOER) and *Larrea tridentada* (LATR) were transferred to chile seedlings. Recipient plants and controls were exposed to varied levels of added salt. Biomass of untreated plants declined proportionally to salt exposure. However, BOER endophyte treated plants maintained productivity as salt increased. LATR endophyte treated plants were most productive in the high-salt treatments. Results indicate that endophytes present in BOER and LATR can modify the salt tolerance of chile plants.
Figure 13:
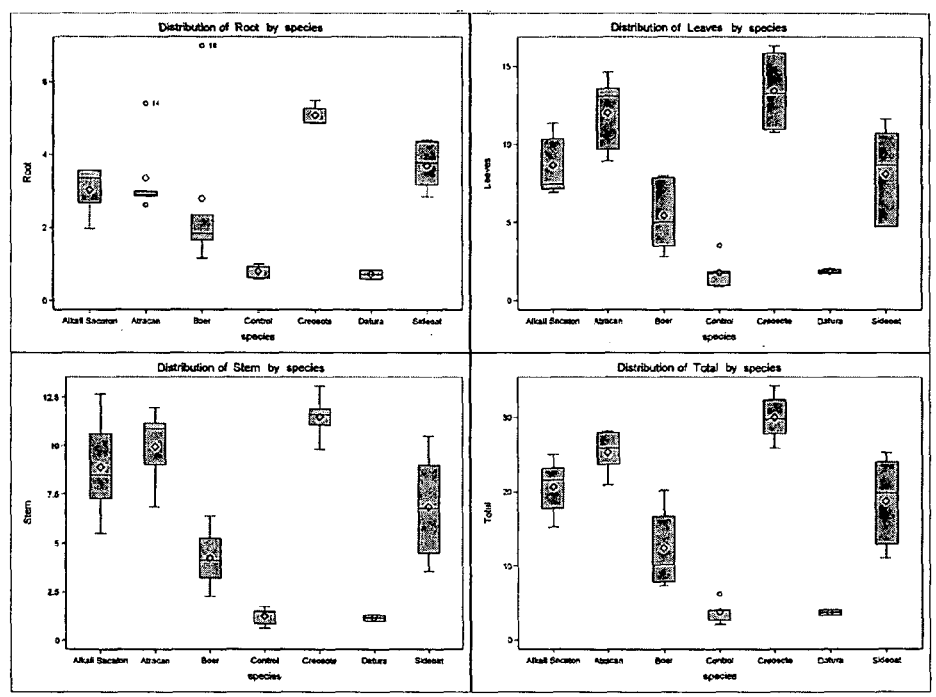
FIG. 13 shows the results of tomato plants (n=5) treated with endophytes from six species of desert range plants, cultivated for six weeks, and measured for differences in root biomass, number of leaves, stem height, and total plant biomass. Endophytes were transferred from *Sporobolus airoides* (alkali sacaton), *Atriplex canescens* (Atracan), *Bouteloua eriopoda* (Boer), *Larrea tridentada* (Creosote), *Datura inoxia* (Datura) and *Bouteloua curtipendula* (Sideoat). This study illustrates endophyte-specific changes may differ even between endophyte donors from the same genus (Bouteloua and Sporobolus), and demonstrates that in some cases, endophytes may decrease plant performance, as was seen for tomato treated with datura endophytes.
Figures 14A, 14B:
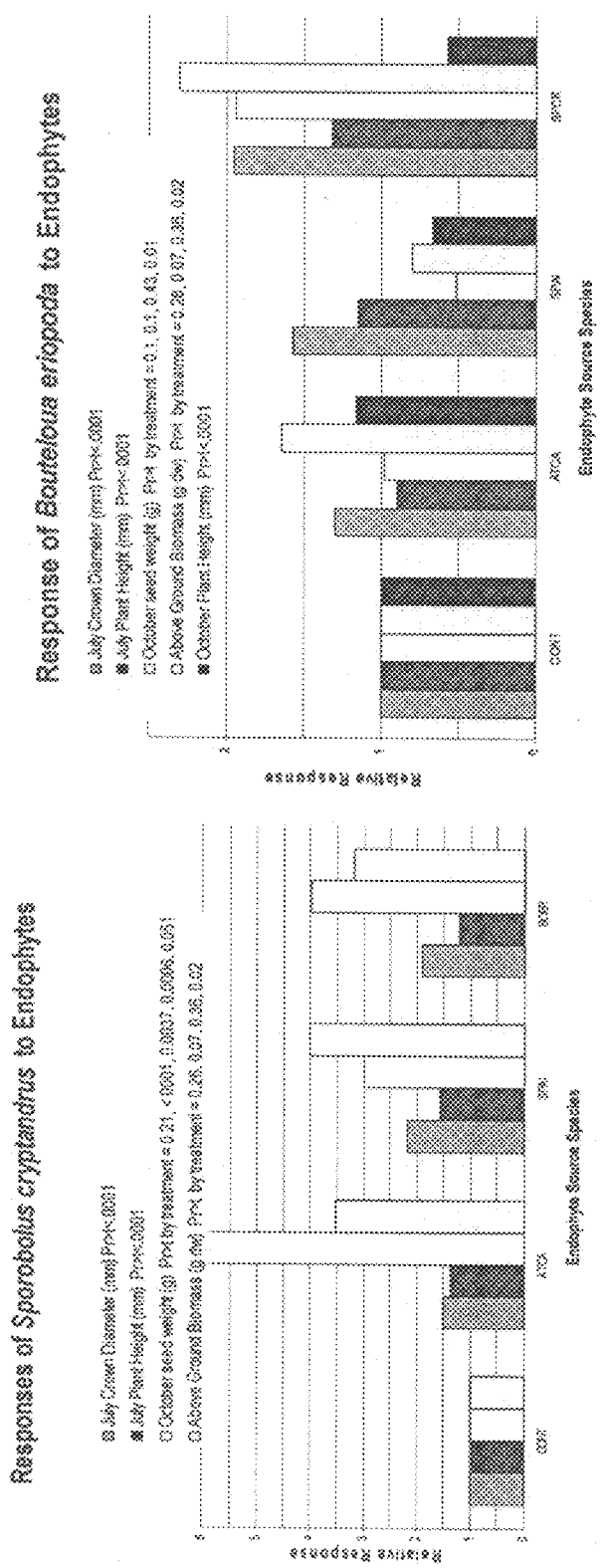
FIGS. 14 (*a*) and (*b*) show the responses of *Sporobolus cryptandrus* and *Bouteloua eriopoda* to endophytes. Field persistence of endophyte induced changes in plant vigor. The graph below represents data collected from field plots consisting of endophyte treated and untreated sand dropseed (SPCR) and black grama (BOER). Endophytes from each species or from fourwing saltbush (ATCA) or alkali sacaton (SPAI) were transferred to BOER and SPCR seedlings. Seedlings were greenhouse hardened, then transferred to field plots in a randomized block design. Each treatment contained 3 replicated subplots with 16 plants per subplot. Significant differences were seen in plant height, crown diameter, above ground biomass, and seed production. Viability of harvested seed was examined, but no endophyte-specific differences were observed. Sand dropseed seeds from all treatments exhibited approximately 90% viability. Viability for black grama seeds was 40%.

The chromatograms in FIG. 9 represent gas chromatogram/mass spectrometer (GC/MS) profiles of chloroform or methanol extractable compounds from leaves of tomato and tomato inoculated with endophytes from *Datura inoxia*. The chromatograms of the two chloroform extracts are set to the same scale (15 Mcounts); the chromatograms for the methanol extracts are also set to the same scale (4 Mcounts). Chromatograms suggest quantitative and qualitative differences in a number of compounds Alkaloids characteristic of *Datura*, such as scopalmine, were looked for and not detected. This experiment suggests that transferred endophytes may be used to alter plant chemistry. As such, the technology could have implications for development of pharmaceuticals and nutriceuticals, altering nutritional value of plants, and developing plants with enhanced abilities for xenobiotic transformation.

Example 4

The experiments in Examples 1-3 were repeated to examine the physical effects of the transfer endophytic fungi between a variety of donor and recipient plants shown in Table 1. The sole exception was the transfer of endophytes to watermelon, wherein the endophytes were transferred by injection of an extract prepared from callus of the fourwing saltbush. Approximately 10 g of callus was ground with a mortar and pestle in cold phosphate buffered saline, passed through a sieve and a 0.4µ filter, and the filtrate concentrated by centrifugation to provide 10 ml. of concentrate. One ml doses of concentrate were injected into the stems or nodes of watermelon seedlings. In the remaining plants shown in the table, seeds were surface disinfected, and germinating seedlings were placed in contact with callus from donor plants and recovered as described in Example 1. Donor plants used were *Atriplex canescens* (ATCA), *Atriplex griffithsii* (ATGR), *Bouteloua curtipendula* (BOCU), and *Larrea tridentada* (LATR). The results are shown in Table 1.

It is understood that the foregoing detailed description is given merely by way of illustration and that modifications and variations may be made therein without departing from the spirit and scope of the invention.

TABLE 1

| Plant Common Name | Family | Genus | Species | Measured Variable | Endophyte Source* | Treated Value | Control | Trt/Cont | Pr > F | Comment |
|---|---|---|---|---|---|---|---|---|---|---|
| Watermelon | *Cucurbitaceae* | *Citrullus* | *lanatus* | Root Dry Wt. | ATCA | 0.12 | 0.08 | 1.42 | 0.0064 | Significant. Fungal propagules from plant extracts were injected by syringe. |
| Strawberry | *Rosaceae* | *Fragaria* | | Root Dry Wt. | ATCA | 0.53 | 0.59 | 0.89 | 0.4044 | Difference not significant. However, all plants were growth restricted at time of harvest. |

TABLE 1-continued

| Plant Common Name | Family | Genus | Species | Measured Variable | Endophyte Source* | Treated Value | Control | Trt/Cont | Pr > F | Comment |
|---|---|---|---|---|---|---|---|---|---|---|
| Carrot | Apiaceae | Daucus | carota | Root Dry Wt. | ATGR | 7.54 | 3.63 | 2.08 | 0.0460 | Significant |
| Cotton | Malvaceae | Gossypium | hirsutum | Root Dry Wt. | ATCA | 4.00 | 4.11 | 0.97 | 0.5249 | Difference not significant |
| Tomato | Solanaceae | Lycopericon | esculentum | Root Dry Wt. | ATCA | 3.35 | 0.80 | 4.18 | <0001 | Highly significant differences between treatments |
| Mexican Primrose | Onagraceae | Oenothera | berlandieri | Root Dry Wt. | ATCA | 0.48 | 0.14 | 3.35 | 0.0162 | Significant differences |
| Lettuce | Asteraceae | Lactuca | sativa | Total DW | ATCA | | | | | No significant difference in biomass. Three varieties (an iceburg, loose leaf, and romaine) were evaluated. |
| Papaya | Caricaceac | Carica | papaya | | ATCA | | | | | In progress. Treated plants appear significantly larger than untreated but have not been measured. |
| Wolfberry | Solanaceae | Lycium | chinense | | ATCA | | | | | In progress. No differences between treatment and control are apparent |
| Maple | Aceraceae | Acer | | | ATCA | | | | | In progress. No differences between treatment and control are apparent |
| Sand dropseed | Poaceae | Sporobolus | cryptandrus | Crown Diameter | SPCR | 1.58 | 1.57 | 1.01 | 0.0900 | Significant differences |
| Sand dropseed | Poaceae | Sporobolus | cryptandrus | Crown Diameter | SPCR | 2.01 | 1.57 | 1.28 | 0.0900 | Significant differences |
| Tobacco | Solanaceae | Nicotiana | tabacum | Clorophyll Content | BOER | 10.47 | 5.82 | 1.80 | 0.0010 | Significant differences |
| Tobacco | Solanaceae | Nicotiana | Tabacum | Fresh Weight | ATGR | 2.68 | 1.55 | 1.73 | 0.0350 | Significant differences |
| Brassica | Brassicaceae | Brassica | rapa | Chlorophyll ug/ml extract | ATCA | 930.21 | 688.91 | 1.35 | 0.0010 | Significant differences |
| Sorghum | Poaceae | Sorghum | bicolor | Root Length | BOER | 6.00 | 2.70 | 2.22 | 0.0050 | Significant differences. see image. |
| Eastern Gamegrass | Poaceae | Trysacum | dactiloides | Root Length | BOER | 7.46 | 3.50 | 2.13 | 0.0050 | Significant differences |

ATCA = *Atriplex canescens*
BOER = *Bouteloua eriopoda*
ATGR = *Atriplex griffithsii*
SPCR = *Sporobolus cryptandrus*

We claim:

1. A plant material comprising a first plant species or part thereof having stably and heritably integrated therein an endophytic fungus derived from a second, different plant species, wherein said first plant species is not a host plant for said endophytic fungus in nature, and further wherein said fungus cannot be isolated and propagated in vitro on culture media.

2. The plant material of claim 1 wherein said fungus is associated with said second plant species in nature and remains associated with said second plant species even when said second plant species is regenerated in vitro from surface disinfected embryonic cells under aseptic tissue culture.

3. The plant material of claim 1 wherein said second plant species is selected from the group consisting of black grama (*Bouteloua eriopoda*, (Torr.) Torr.), sand dropseed (*Sporobolus cryptandrus* (Torr.), alkali sacaton (*Sporobolus airoides* Torr.), fourwing saltbush (*Atriplex canescens*, Pursh Nutt.), and jimson weed (*Datura inoxia* Mill.).

4. The plant material of claim 1 wherein said first plant species is selected from the group consisting of grains, forage, berries, fruit trees, nut trees, forest trees, vegetables, ornamental flouters, shrubs, sugar cane, sugar beets, turf grasses, cotton, *Arabidopsis*, tobacco, and desert grasses.

5. The plant material of claim 4 wherein said first plant species is selected from the group consisting of tomatoes, chiles, onions, wheat, sorghum, cotton, and desert grasses.

6. Seed produced from said plant material of claim 1.

7. The plant material of claim 1 wherein said fungus is heritably transmitted through seed.

8. The plant material of claim 1 wherein said fungus is heritably transmitted through seed and cannot be isolated and propagated in vitro on culture media.

9. The plant material of claim 8 wherein said fungus is associated with said second plant species in nature and remains associated with said second plant species even when said second plant species is regenerated in vitro from surface disinfected embryonic cells under aseptic tissue culture.

10. The plant material of claim 8 wherein said second plant species is selected from the group consisting of black grama (*Bouteloua eriopoda*, (Torr.) Torr.), sand dropseed (*Sporobolus cryptandrus* (Torr.), alkali sacaton (*Sporobolus airoides* Torr.), fourwing saltbush (*Atriplex canescens*, Pursh Nutt.), and jimson weed (*Datura inoxia* Mill.).

11. The plant material of claim 10 wherein said first plant species is selected from the group consisting of grains, forage, berries, fruit trees, nut trees, forest trees, vegetables, ornamental flowers, shrubs, sugar cane, sugar beets, turf grasses, cotton, *Arabidopsis*, tobacco, and desert grasses.

12. The plant material of claim 11 wherein said first plant species is selected from the group consisting of tomatoes, chiles, onions, wheat, sorghum, cotton, and desert grasses.

13. Seed produced from said plant material of claim 8.

\* \* \* \* \*

SEQUENCE LISTING

<160> NUMBER OF SEQ ID NOS: 2

<210> SEQ ID NO 1
<211> LENGTH: 20
<212> TYPE: DNA
<213> ORGANISM: Puccinia triticina

<400> SEQUENCE: 1
gcattcccaa acaactcgac          20

<210> SEQ ID NO 2
<211> LENGTH: 22
<212> TYPE: DNA
<213> ORGANISM: Puccinia triticina

<400> SEQUENCE: 2
cctgtttgag tgtcatgaaa cc          22